United States Patent [19]

Rota

[11] Patent Number: 4,571,185
[45] Date of Patent: Feb. 18, 1986

[54] RETAINING DEVICE FOR REMOVABLE DENTAL PROSTHESES

[76] Inventor: Ennio Rota, 9 Via Della Paglia, I-00153 Roma, Italy

[21] Appl. No.: 716,611

[22] Filed: Mar. 28, 1985

Related U.S. Application Data

[63] Continuation of Ser. No. 543,459, Oct. 19, 1983, abandoned.

[30] Foreign Application Priority Data

Oct. 19, 1982 [IT] Italy .................. 49300 A/82

[51] Int. Cl.⁴ ............................................. A61C 8/00
[52] U.S. Cl. .................................................. 433/173
[58] Field of Search ............... 433/173, 177, 174, 175

[56] References Cited

U.S. PATENT DOCUMENTS

| 717,324 | 10/1902 | Lacy | 433/173 |
| 2,775,816 | 1/1957 | Crevison | 433/117 |
| 3,216,111 | 11/1965 | Sink | 433/177 |
| 3,849,887 | 11/1976 | Brainin | 433/173 |
| 4,379,694 | 4/1983 | Riess | 433/173 |

FOREIGN PATENT DOCUMENTS 0037864 10/1981 European Pat. Off. .

Primary Examiner—Robert Peshock
Attorney, Agent, or Firm—Cushman, Darby & Cushman

[57] ABSTRACT

A device capable of fastening a total or partial, upper or lower, removable dental prosthesis consists of a ball member and a socket member, one of which is fixed in the prosthesis and the other implanted in the alveolar bone, to be engaged on to the other by a snap action.

3 Claims, 6 Drawing Figures

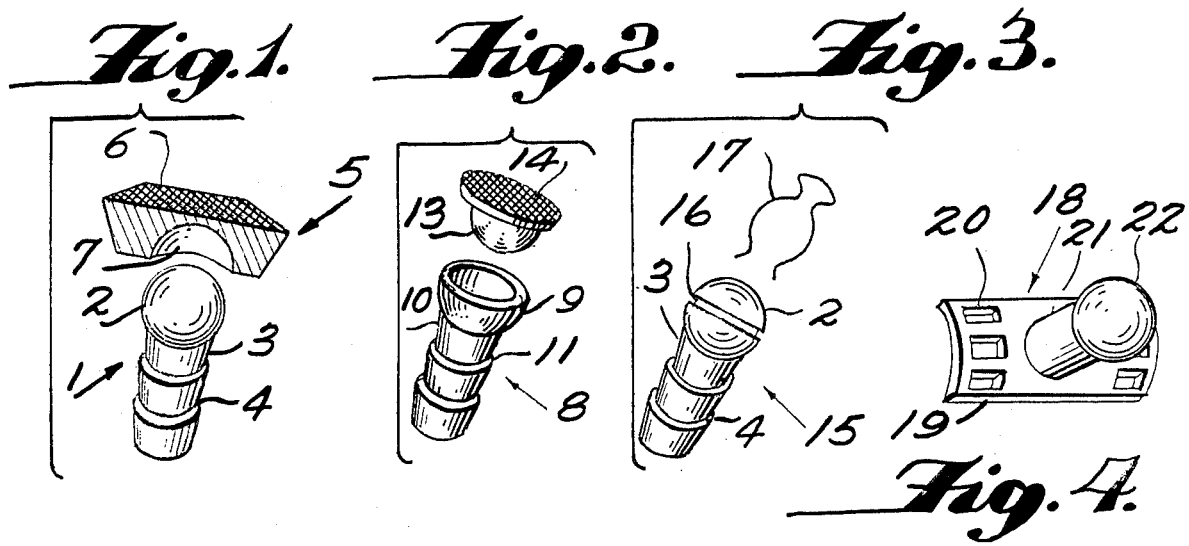
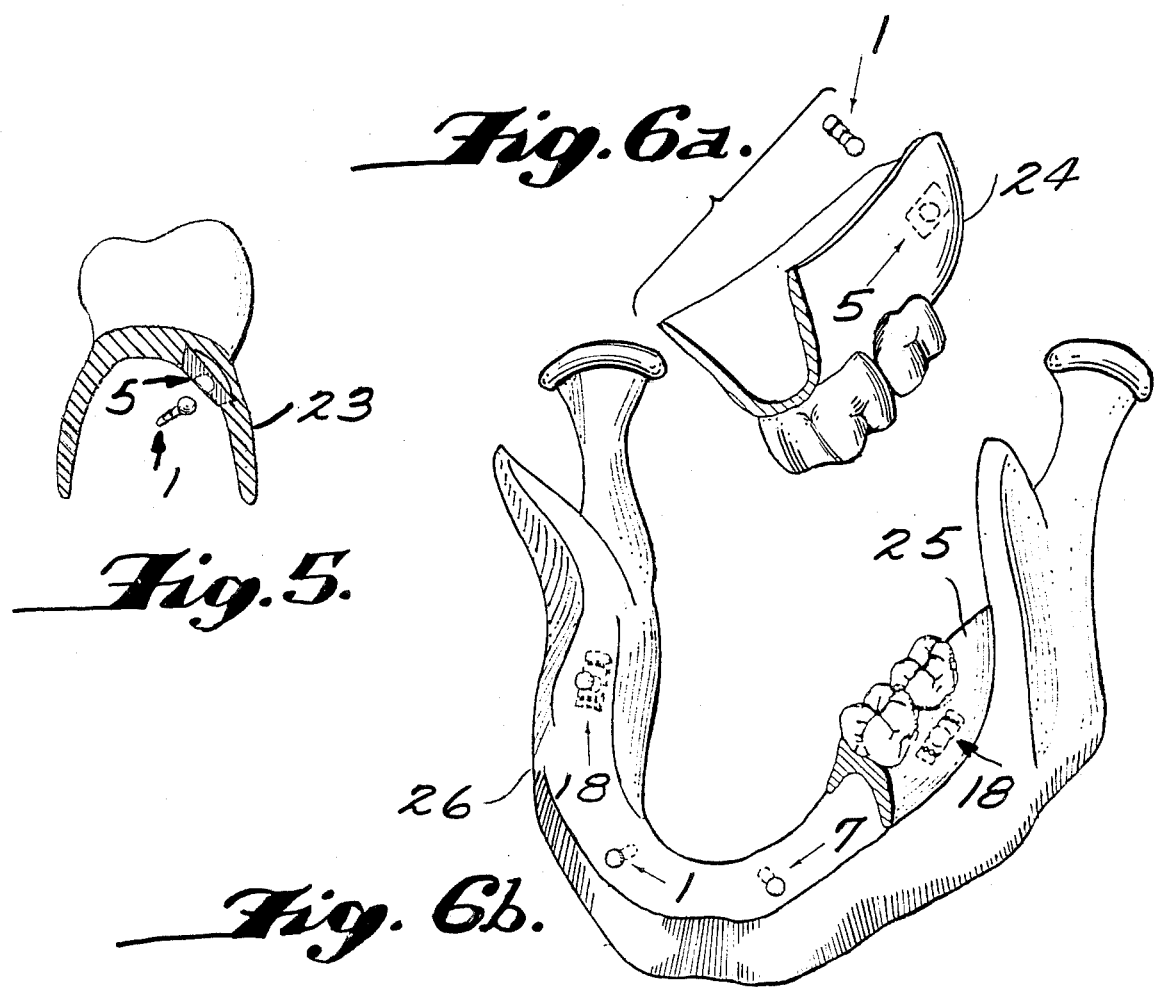

RETAINING DEVICE FOR REMOVABLE DENTAL PROSTHESES

This is a continuation of application Ser. No. 543,459, filed Oct. 19, 1983 which was abandoned upon the filing hereof.

BACKGROUND OF THE INVENTION

The present invention relates to device which can firmly hold in place a dental prosthesis of the removable type.

Currently, a removable prosthesis designed to partially or completely replace one or both of the dental arches is held in place by means of adhesive powders, glues or the like which when ingested tend to cause gastric disturbances. Or alternatively sucking organs are used which not only are precarious in stability especially due to the repeated putting in and taking out of the prosthesis, but also can over the long term lead to carcinogenic epithelial degenerations.

On the other hand permanent implantation of dental prostheses is currently carried out by means of pins, screws or metal lamellae which act as sources of electrolytic or galvanic current leading to reddening and inflammation of the mucosa due to rejection of the implanted metal body. After a few years, the metal degenerates until the implant fails due to a rejection reaction.

Furthermore, in the case of subjects with pronounced reabsorption or even atrophy of the alveolar ridges, removable dental prostheses are deprived of even a modest osteo-mucosa support, so that when applied with conventional methods they are inevitably so mobile and uncontrollable that their use is prevented. The biological-functional and psychological effects these subjects encounter can be readily imagined.

SUMMARY OF THE INVENTION

The aim of the present invention is to provide a surprisingly simple and functional device which can keep a total or partial, lower or upper removable dental prosthesis firmly in place, with the elimination in the latter case of the palate part. Said device is effective in both the presence and absence of a thick alveolar ridge, and completely eliminates the inconveniences mentioned above which are related to conventional techniques for applying the apparatus in question. The device according to the present invention consists essentially of a ball member and a socket member which fit one into the other in a removable fashion, one of the two elements being permanently fixed to the dental prosthesis while the other is implanted in the alveolar bone, to be engaged one to the other by a snap action.

BRIEF DESCRIPTION OF THE DRAWING

The present invention will be better described below in the description of its realizations, shown in an exemplificative and non-limiting way in the attached drawing, in which:

FIG. 1 is a view of one structural embodiment of the device in question;

FIG. 2 is a view of a second structural embodiment of the device;

FIG. 3 is a view of a third structural embodiment of the device;

FIG. 4 is a view of a fourth structural embodiment of the device in which the socket member is not shown but is like that in FIG. 1;

FIG. 5 is a section view of a lower dental prosthesis using the device of FIG. 1; and FIGS. 6a and b are views which illustrate the system for implanting the device in question for removable dental prosthesis, upper and lower respectively (shown partially).

DETAILED DESCRIPTION OF THE PREFERRED EMBODIMENTS

As shown in FIG. 1, the device in question in a first embodiment consists of a ball member, indicated generically with 1, in the form of a pin made of relatively rigid material, preferably non-metallic, consisting of a spherical head 2, in the present example, and a substantially cylindrical shaft 3 with a rough surface as well as a certain number of spaced grooves 4 going around it to ensure its retention in the alveolar bone where it is to be implanted.

The ball member 1 is paired with a socket member indicated generically with 5, consisting of an insert 6 of resilient material shaped essentially like a truncated cone, with an essentially semispherical hollow 7 having the shape of the head 2 of the ball member 1, which to be fixed to the inner surface of the dental prosthesis in a suitable cavity in a position corresponding to that where the ball member 1 is implanted in the alveolar bone.

FIG. 2 shows a second embodiment of the device in question in which the part destined to be implanted in the alveolar bone is a socket member, indicated generically with 8, of relatively rigid material, preferably non-metallic, consisting of a semispherical cupped head 9 connected to a shaft 10 with a rough surfaces and grooves 11 around it for the reasons discussed above. The part to be mounted on the dental prosthesis consists of a ball member indicated generically with 12, shaped like a substantially semispherical body 13 of a relatively rigid material, preferably non-metallic, connected to a support 14 of elastic material to secure in a corresponding cavity made in the dental prosthesis.

FIG. 3 shows a third realization of the device according to the present invention consisting of a ball element indicated generically with 15, of relatively rigid, preferably non-metallic, material, of the same pin-like shape as that of FIG. 1, in which the same reference numbers are used to indicate the same parts with no further illustration, with the sole difference that the spherical head 2 has a depression 16 running around it. There is a socket element 17 consisting of a spring clamp whose closed end is incorporated permanently in the dental prosthesis in such an orientation that the two curved openable legs, when said prosthesis is put in, are in correspondence with the depression 16 in the head of ball element 15, implanted in the alveolar bone, to reciprocally engage each other.

With reference to FIG. 4, a fourth realization of the device according to the present invention in shown, but only the ball element since the socket element (not shown) is completely identical to that indicated generically with 5 in FIG. 1.

The ball element in the realization in FIG. 4, indicated generically with 18, of relatively rigid, preferably non-metallic material, was designed for use in implantations in the alveolar bone, both above and below the periosteum, in cases where the alveolar ridge is insufficient or lacking altogether. It consists of a widened saddle-shaped base to better distribute and so altenuate the chewing force, with a certain number of openings 20 to improve shaft 27 with a spherical head 22 on the end protruding from the top face in the center.

It should be specified that the components 1, 8 and 15 of the devices in the first, second and third realizations of the present invention in FIGS. 1, 2 and 3 should be inserted into the alveolar bone at a direction oblique or transverse to the chewing axis to allow efficient retention of said components without their being too long.

FIGS. 5 and 6 show examples of the application of the device according to the present invention.

In particular, FIG. 5 shows the installation of a socket member 5 of the device in FIG. 1 in a suitable cavity made in the inner wall of the lower dental prosthesis 23 in a position such that the hollow 7 is placed properly for the orientation of the ball element 1, as shown in FIG. 1, in order to ensure easy and reciprocal engagement when the latter is inserted in the alveolar bone (not shown) in the preferential directions cited above.

In FIG. 6a, 24 is a portion of an upper dental prosthesis with its inner wall bearing, in the manner described above, a socket element 5 of the device in FIG. 1, which will engage a ball element 1 shown in the orientation provided upon implantation in the alveolar bone (not shown). In FIG. 6a, 25 is a portion of a lower dental prosthesis applied by means of the device in FIG. 4 to the corresponding alveolar bone 26. The ball elements 1 of the two device as in FIG. 1 are also implanted on said bone, as is a second device 18 as in FIG. 4, placed so that the corresponding socket elements on the remaining part (not shown) of the dental prosthesis 25 engage easily upon application of the latter.

With regard to the materials of which the relatively rigid, non-metallic, components of the various realizations described above for the device in question, appropriate biocompatible resins of suitable hardness should preferably used, with a without completely incorporated metal inserts to increase strength; a particularly preferred resin is Teflon, while the resilient parts should be of sufficiently resilient and hard biocompatible rubbers to prevent trauma and related inflammation of the gums. To this end, a practical and effective method is described below for making the socket member of the device shown in FIG. 1: said method consists of the operations of pouring the selected rubber in the fluid state in the cavity mentioned above made in the inner wall of the dental prosthesis until it is full, making the hollow 7 by imprinting the head 2 of the ball element 1, leaving the poured rubber solidify so that the plug 5 complete with bollow 7 is solidly placed in said cavity in the prosthesis.

The structural technical characteristics, as well as those of the materials with which the device according to the invention, are such that they guarantee not only the great aspiration of wearers of removeable dental prosthesis, that is, to have a stable and well-fixed prosthesis even with no teeth, but also at least three other advantages of not insignificant importance: the first derives from the fact that, since the member of the device implanted in the alveolar bone is applied underneath the mucosa, there is no communication between it and the oral environment and so there is no infiltration of the bacterial flora, a major cause of inflammatory and infective phenomena; the second advantage derives from the fact that since the device in question is realized preferably with a non-metallic material, it generates no electrolytic or galvanic current as it would if it were made of metal, which because of its nature and the environment in which it is found would lead to weak currents which cause inflammation of the surrounding mucosa and degeneration of the underlying bone; the third advantage derives from the fact that since the material of which the elements implanted in alveolar bone is not rigid or hard like metal, the pressures and forces of chewing are greatly reduced due to its relative elasticity and that of the socket in which it is inserted, leading to attenuated effects on the underlying biological tissue.

The device according to the invention may be applied to new prostheses as well as to old ones already made with other systems, in the latter case eliminating further expense to the patient.

The present invention is not limited to the examples described, but includes any variation in execution.

I claim:

1. A method of removably attaching a dental prosthesis in a patient's mouth comprising: providing an implant having a head part and a substantially cylindrical roughened shaft part formed of relatively rigid biocompatible resin; implanting the shaft part in the patient's alveolar bone in a direction oblique or transverse to the chewing axis such that the head part is exposed; forming a cavity in an inner wall of a dental prosthesis; inserting into the cavity a mass of biocompatible resilient rubber material in the fluid state; imprinting the head part in the fluid rubber material to thereby form therein a recess which is complementary to the head; and allowing the rubber material to solidify.

2. In a method of attaching a dental prosthesis in a patient's mouth with the aid of an implant embedded in the patient's alveolar bone, the implant having an exposed head part and a substantially cylindrical roughened shaft part, the improvement comprising forming a cavity in an inner wall of a dental prosthesis; inserting into the cavity a mass of biocompatible resilient rubber material in the fluid state; imprinting the head part in the fluid rubber material to thereby form therein a recess which is complementary to the head; and allowing the rubber material to solidify.

3. A method as in claim 1 wherein the shaft part of the implant is embedded in the alveolar bone in a direction oblique or transverse to the chewing axis.

* * * * *